(12) United States Patent
Tahmasebi Maraghoosh et al.

(10) Patent No.: US 10,595,816 B2
(45) Date of Patent: Mar. 24, 2020

(54) SYSTEM AND METHOD FOR TRACKING A PENETRATING INSTRUMENT

(71) Applicant: KONINKLIJKE PHILIPS N.V., Eindhoven (NL)

(72) Inventors: Amir Mohammad Tahmasebi Maraghoosh, Ridgefield, CT (US); Guy Gerard Marie Vignon, Croton on Hudson, NY (US); Ameet Kumar Jain, New York, NY (US)

(73) Assignee: KONONKLIJKE PHILIPS N.V., Eindhoven (NL)

( * ) Notice: Subject to any disclaimer, the term of this patent is extended or adjusted under 35 U.S.C. 154(b) by 938 days.

(21) Appl. No.: 15/105,146

(22) PCT Filed: Dec. 16, 2014

(86) PCT No.: PCT/IB2014/066943
§ 371 (c)(1),
(2) Date: Jun. 16, 2016

(87) PCT Pub. No.: WO2015/092667
PCT Pub. Date: Jun. 25, 2015

(65) Prior Publication Data
US 2016/0317119 A1 Nov. 3, 2016

Related U.S. Application Data

(60) Provisional application No. 61/918,895, filed on Dec. 20, 2013.

(51) Int. Cl.
*A61B 8/00* (2006.01)
*A61B 8/08* (2006.01)
(Continued)

(52) U.S. Cl.
CPC ............ *A61B 8/0841* (2013.01); *A61B 5/066* (2013.01); *A61B 6/032* (2013.01); *A61B 8/085* (2013.01);
(Continued)

(58) Field of Classification Search
CPC ....... A61B 8/0841; A61B 34/20; A61B 5/066; A61B 6/032; A61B 8/085; A61B 8/12; A61B 8/463; A61B 8/466
See application file for complete search history.

(56) References Cited

U.S. PATENT DOCUMENTS 4,249,539 A 2/1981 Vilkomerson
4,697,595 A 10/1987 Breyer
(Continued)

FOREIGN PATENT DOCUMENTS

RU 2256169 C1 7/2005
WO 2012066470 A1 5/2012
WO 2013001437 A1 1/2013

OTHER PUBLICATIONS

Wein, W. et al "Automatic CT-Ultrasound Registration for Diagnostic Imaging and Image-Guided Intervention", Medical Image Analysis, vol. 12, No. 5, 2008, pp. 577-585.

*Primary Examiner* — Joel Lamprecht

(57) ABSTRACT

A system for tracking an instrument including an intraoperative transducer array configured to generate signals from array positions to generate real-time images of an area of interest. The instrument can be a penetrating instrument having a sensor mounted at a position of interest and being responsive to the signals from the array positions. A signal processing module can be provided and configured to determine a position and orientation of the instrument in accordance with the signals and to classify media of the position of interest based upon a response of the sensor to the signals from the array positions. An overlay module can be provided (Continued)

and configured to generate an overlay image registered to the real-time images to identify a position of the position of interest and provide feedback on the media in which the position of interest is positioned. A display can be provided and configured to provide visual feedback of the overlay image on the real-time images.

20 Claims, 5 Drawing Sheets

(51) Int. Cl.
*A61B 8/12* (2006.01)
*A61B 5/06* (2006.01)
*A61B 34/20* (2016.01)
*A61B 6/03* (2006.01)
*A61B 17/34* (2006.01)
*A61B 90/00* (2016.01)

(52) U.S. Cl.
CPC ............... *A61B 8/12* (2013.01); *A61B 8/463* (2013.01); *A61B 8/466* (2013.01); *A61B 8/467* (2013.01); *A61B 8/483* (2013.01); *A61B 8/5238* (2013.01); *A61B 8/5261* (2013.01); *A61B 34/20* (2016.02); *A61B 8/5246* (2013.01); *A61B 2017/3413* (2013.01); *A61B 2034/2063* (2016.02); *A61B 2090/364* (2016.02); *A61B 2090/378* (2016.02)

(56) References Cited

U.S. PATENT DOCUMENTS

| 6,048,312 | A | 4/2000 | Ishrak |
| 7,068,867 | B2 * | 6/2006 | Adoram ............... A61B 8/0833 |
| | | | 385/12 |
| 8,099,155 | B2 | 1/2012 | Boese |
| 2003/0171677 | A1 | 9/2003 | Marmarelis |
| 2004/0131299 | A1 | 7/2004 | Adoram |
| 2006/0241450 | A1 | 10/2006 | Da Silva |
| 2006/0253107 | A1 | 11/2006 | Hashimshony |
| 2013/0218024 | A1 | 8/2013 | Boctor |

* cited by examiner

SYSTEM AND METHOD FOR TRACKING A PENETRATING INSTRUMENT

CROSS-REFERENCE TO PRIOR APPLICATIONS

This application is the U.S. National Phase application under 35 U.S.C. § 371 of International Application No. PCT/IB2014/066943, filed on Dec. 16, 2014, which claims the benefit of U.S. Provisional Patent Application No. 61/918,895, filed on Dec. 20, 2013. These applications are hereby incorporated by reference herein.

BACKGROUND

Technical Field

This disclosure relates to medical instrument guidance systems and methods, and more particularly to needle guidance using smart needles and images fused to provide greater visualization of the needle guidance.

Description of the Related Art

The past decade has seen an increase in use of ultrasound in epidural interventions, with predictions that it would soon be part of the standard of clinical care. However, one challenge for ultrasound guided epidurals is the difficulty in seeing the needle without crossing into the spine. Physicians primarily rely on the loss of resistance to detect this passage, a highly subjective maneuver, possibly leading to complications. Spine-related pain has been a common cause of morbidity. Back pain along with the substantial medical costs of diagnosis and treatment has imposed a burden and productivity loss. An epidural injection is one of many methods being considered to relieve pain, along with physical therapy, oral medications and surgery if a patient is not responding to conservative treatments. An epidural injection is delivered into the epidural space of the spine to provide temporary or prolonged relief from pain or inflammation.

Three layers of tissue cover the spinal cord. An epidural space is the area of space between an outermost tissue layer (dura) of the spinal cord and an inside surface of bone and supporting ligaments in which it is contained. The epidural space runs the length of the spine. The epidural space contains fat tissue along with blood vessels and nerve roots. An epidural injection may be performed to alleviate pain caused by a herniated or bulging disk, spinal stenosis, post-operative "failed back" surgery syndromes (chronic back or leg pain after spinal surgery), or other injuries to spinal nerves, vertebrae and surrounding tissues.

Epidural anesthesia is also administered for births and for many surgical procedures. Complications of administering epidural anesthesia arise due to incorrect needle positioning during the injection but rarely cause any permanent damage to the patient. However, the complications could be reasonably disconcerting and could persist for several days. During epidural anesthesia, the placement of the needle is important to effectively administer pain relief and avoid nerve damage. However, accurate epidural needle insertion is difficult to learn and typically relies on the expertise of an anesthesiologist to detect a loss of resistance on the needle plunger to determine placement.

Portable ultrasound is increasingly used to help needle positioning for epidural and other injections or spinal taps and other biopsies, especially in the presence of challenging anatomies (high body mass index (BMI), scoliosis, etc.). However, ultrasound does not visualize the needle tip well especially for procedures where needle insertion is very steep. Also, tissues (e.g., ligamentum flavum) may be difficult to see even with ultrasound guidance due to the challenging environment for ultrasound (e.g., the presence of bones).

Needle visualization such as electromagnetic tracking has been demonstrated to highlight the needle tip on an ultrasound image, and products are available for anesthesia and biopsy guidance. However, the high expense of these needles and the cumbersome setup time has attenuated the adoption of this technology. Other ways to improve needle visualization include the addition of another imaging modality to the workflow such as X-ray or even computed tomography (CT), but this makes the procedure significantly more cumbersome.

SUMMARY

In accordance with the principles of the present disclosure, a system for tracking a penetrating instrument includes an intraoperative transducer array configured to generate signals from a plurality of array positions to generate one or more real-time images of an area of interest. A penetrating instrument has a body with a sensor mounted at a position of interest on the body. The sensor is responsive to the signals from the plurality of array positions. A signal processing module is configured to determine a position and orientation of the penetrating instrument in accordance with the signals from the plurality of array positions. The signal processing module is further configured to classify media in which the position of interest is positioned based upon a response of the sensor to the signals from the plurality of array positions. An overlay module is configured to generate an overlay image registered to the one or more real-time images to identify a position of the position of interest and provide feedback on the media in which the position of interest is positioned. A display is configured to provide visual feedback of the overlay image on the one or more real-time images.

Another system for tracking a penetrating instrument according to principles of the present disclosure includes a signal processing module configured to determine a position and orientation of a penetrating instrument in accordance with signals from a plurality of array positions. The penetrating instrument has an ultrasound sensor mounted at or near a distal tip position. The signal processing module is further configured to classify a tissue type in which the tip of the penetrating instrument is positioned based upon a response of the sensor to the signals from the plurality of array positions.

This system can also include an intraoperative ultrasound transducer array configured to generate the signals from the plurality of array positions to provide one or more real-time images of an area of interest. Also included in the system can be an overlay module configured to generate an overlay image registered to the real-time images. The overlay image can include a highlighted position of the penetrating instrument and an identification of the tissue type. A display can also be included and configured to provide visual feedback of the overlay image on one or more of the real-time images. One or more of the real-time images can include one or more two-dimensional images. The system can further include a three-dimension reconstruction module configured to reconstruct a three-dimensional image volume of the area of interest from one or more of the two-dimensional images. In addition, the system can include a registration module configured to register one or more two-dimensional real-time images to the three-dimensional image volume of the area of interest. It is also possible that the registration module is configured to register a reference image to the three-dimensional image volume of the area of interest. The penetrating instrument can be or include a needle. The tissue type can be employed as an indicator as to when material should be injected through the penetrating instrument. The penetrating instrument can be employed for an epidural intervention.

Yet another system for tracking a penetrating instrument according to principles of the present disclosure include an intraoperative ultrasound transducer array configured to generate signals from a plurality of array positions to provide one or more real-time images of an area of interest. A needle has an ultrasound sensor mounted at a distal tip position. The sensor is responsive to the signals from the plurality of array positions. A signal processing module is configured to determine a position and orientation of the needle in accordance with the signals from the plurality of array positions. The signal processing module is further configured to classify a tissue type in which a tip of the needle is positioned based upon a response of the sensor to the signals from the plurality of array positions. An overlay module is configured to generate an overlay image registered to the one or more real-time images. The overlay image includes a highlighted position of the needle and an identification of the tissue type. A display is configured to provide visual feedback of the overlay image on the one or more real-time images.

A method for tracking a penetrating instrument according to the present disclosure includes generating signals from a plurality of array positions to generate one or more real-time images of an area of interest; providing a penetrating instrument having a body with a sensor mounted at a position of interest on the body, the sensor being responsive to the signals from the plurality of array positions; determining a position and orientation of the penetrating instrument in accordance with the signals from the plurality of array positions using a signal processing module; classifying media in which the position of interest is positioned based upon a response of the sensor to the signals from the plurality of array positions; generating an overlay image registered to the one or more real-time images to identify a position of the position of interest and provide feedback on the media in which the position of interest is positioned; and displaying the overlay image on the one or more real-time images.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
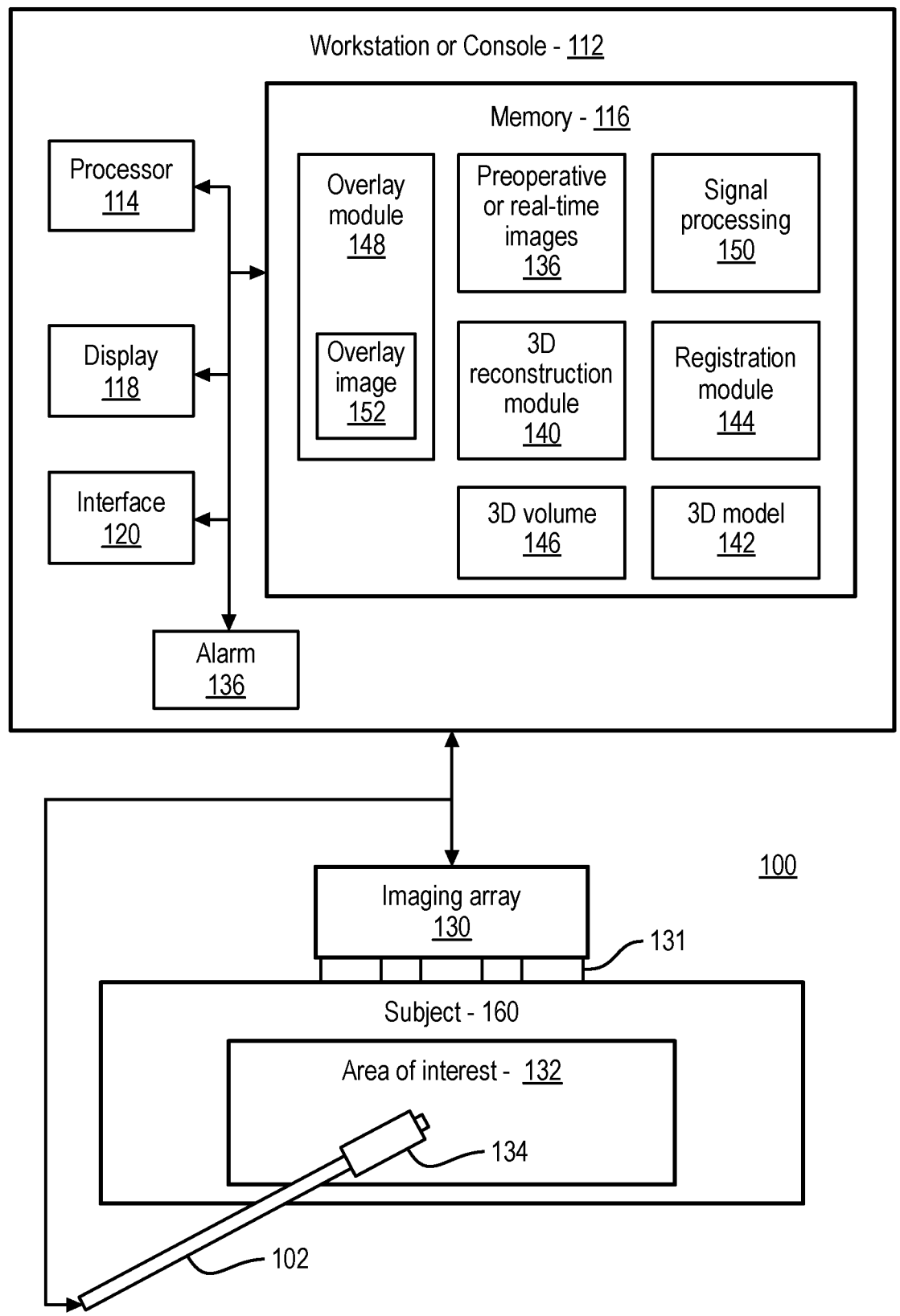
FIG. 1 is a block/flow diagram showing a penetrating instrument tracking system in accordance with one embodiment.

In accordance with the present principles, systems and methods are provided, which assist in navigating a needle or other guided instrument and improve clinical outcomes in epidural or other interventions. The present principles are cost-sensitive and provide benefits in this regard by employing a variety of low-cost modules. The low-cost modules or tools may include, e.g., smart needles that can be visible in ultrasound (US) images, procedure planning tools, 3D volume reconstruction tools using 2D image sweeps, registration tools of patient to computed tomography (CT) images, registration tools of statistical-models of the spine to a patient 3D plan, live 2D-3D registration tools of a current ultrasound image, 3D live needle positioning tools according to a plan. Embodiments may employ one or more of the above modules or tools.

In one embodiment, one or more ultrasound sensors are placed near a tip of a needle. The sensor enables needle tip visualization as it receives signals from an imaging probe. This helps to track a current position and orientation of the needle, making sure the needle does not penetrate sensitive spinal tissue. Additionally, before a procedure, a quick 1D sweep in the elevation direction of a linear probe can be used to construct a 3D volume of the patient spinal anatomy using, e.g., speckle correlation methods. This volume can be then registered to a statistical model (or pre-operative CT images) of a vertebrae, improving the 3D understanding of the anatomy before the intervention. The live US image can now be registered to this 3D plan using, e.g., a slice-volume fusion algorithm. As the needle is now inserted into the patient, it can be tracked in 3D using needle tracking technology in accordance with the present principles and visualized on top of the 3D plan. This system significantly reduces complications and increases efficacy.

Epidural anesthesia procedures were conventionally performed in a relatively blind fashion. For example, anatomic landmarks were palpated, and trigger point injections were completed either with anesthetic or anesthetic mixed with steroid preparations. More recently, image-based needle-guidance has been employed, which allows selective placement of medication further aiding in diagnosis and treatment. Pre-operative imaging, such as, CT, is available so that the fusion of pre-operative imaging with intra-operative ultrasound can aid ultrasound interpretation and guidance. However, such image-based needle guidance can be quite complicated as the interpretation of ultrasound can be difficult because of the presence of imaging artifacts and complexity of the ultrasound echoes from the spinal anatomy. The present principles offer precise localization of a needle tip on the ultrasound image for spatial guidance. This will improve the outcomes of such procedures and reduce complications. Conveniently, only one sensor may be used on the needle for easy manufacturing and maintaining low needle cost.

The present principles build on in-situ needle tracking where an ultrasound sensor is embedded in the needle close to the tip and, as it receives beams from an external ultrasound imager, receives and analyzes these signals to output precise localization of the needle tip in the frame of reference corresponding to the ultrasound image.

It should be understood that the present embodiments will be described in terms of epidural injections as an example. However, the described technology is applicable to many other procedures in anesthesia, pain management, and cancer care, e.g., biopsies.

It also should be understood that the present invention will be described in terms of medical instruments; however, the teachings of the present invention are much broader and are applicable to any guided instruments. In some embodiments, the present principles are employed in tracking instruments for biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Referring now to the drawings in which like numerals represent the same or similar elements and initially to FIG. 1, a system 100 for instrument guidance is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 stores a plurality of modules configured to interpret imaging and other feedback signals to determine a position of an instrument relative to a target or plan and with respect to surrounding features (or tissues in an interventional environment).

Memory 116 includes a 3D volume reconstruction module 140 for reconstructing a 3D volume(s) 146 from 2D intraoperative images, e.g., ultrasound images. In one embodiment, 3D intraoperative images may be collected and included in the 3D volume 146. The 3D volume reconstruction module 140 may include reconstruction algorithms or methods that employ a plurality of 2D images to build the 3D volume 146. Such algorithms may include speckle correlation methods or other techniques. In one embodiment, a 3D statistical model or models 142 are provided for an area of interest 132. These models 142 may include preoperative image volumes, e.g., pre-op CT images, of the area of interest or features within the area of interest, e.g., the vertebrae for an epidural injection procedure.

A registration module 144 may register a 3D reconstructed volume (from module 140) to a statistical atlas or pre-op CT model 142. In one embodiment, the registration module 144 identifies features or feature vectors in each image, reconstruction or model and aligns the features to provide registration therebetween. Other registration methods may also be employed.

An intraoperative imaging transducer array 130 (e.g., ultrasound, although other imaging devices may be employed) are provided for scanning the area of interest 132 in a subject 160 (e.g., a patient, a module, device, etc.). An instrument 102 subject to guidance in accordance with the present principles may include a needle, a catheter, a guidewire or any other guidable instrument. One or more single-element transducers 134 are inserted in the instrument 102 in a position of interest, e.g., at or near a tip of a needle used for epidural injection.

The single-element transducer(s) 134 are employed during a procedure to determine a type of tissue the instrument 102 (e.g., needle) is currently passing through or in contact with. This feature provides relevant information in real-time (in-situ) to an operator or technician to provide feedback as to where the needle (102) is penetrating and to provide an indicator when the needle has reached its target depth or position. In addition, an alarm 136 may be triggered in the instance when the needle experiences an unexpected change or varies from a planned trajectory or depth.

The registration module 144 includes an image-based algorithm for registering 2D real-time US images, taken by transducers 131 of the transducer array 130, to the reconstructed 3D volume 146. An overlay module 148 is configured to overlay real-time tip positions of the instrument 102 on an image, such as the 3D volume, on an atlas or model 142 or on pre-op CT images. The needle 102 can be visualized on top of a 3D plan or image (model) 142 using an overlay image 152 and a signal processing module 150.

The overlay image 152 may provide indications of the tissue type or other data relevant to the needle trajectory and depth.

The overlay module 148 generates the tip position in the real-time images and displays the same on a graphical user interface (GUI) such as a display 118. The overlay module 148 receives image data from one or more images, atlas or model and indicates a position of the transducer in the image(s), atlas or model. The overlay image 152 is accurately registered with a background image(s), atlas or model to display a position of the instrument 102 in the region of interest 132. The signal processing module (or algorithm) 150 determines the position and orientation of the instrument 102 within the area of interest 132.

Workstation 112 includes the display 118 for viewing internal images of the subject 160 (patient or volume) and the overlay image 152. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Figure 2B:
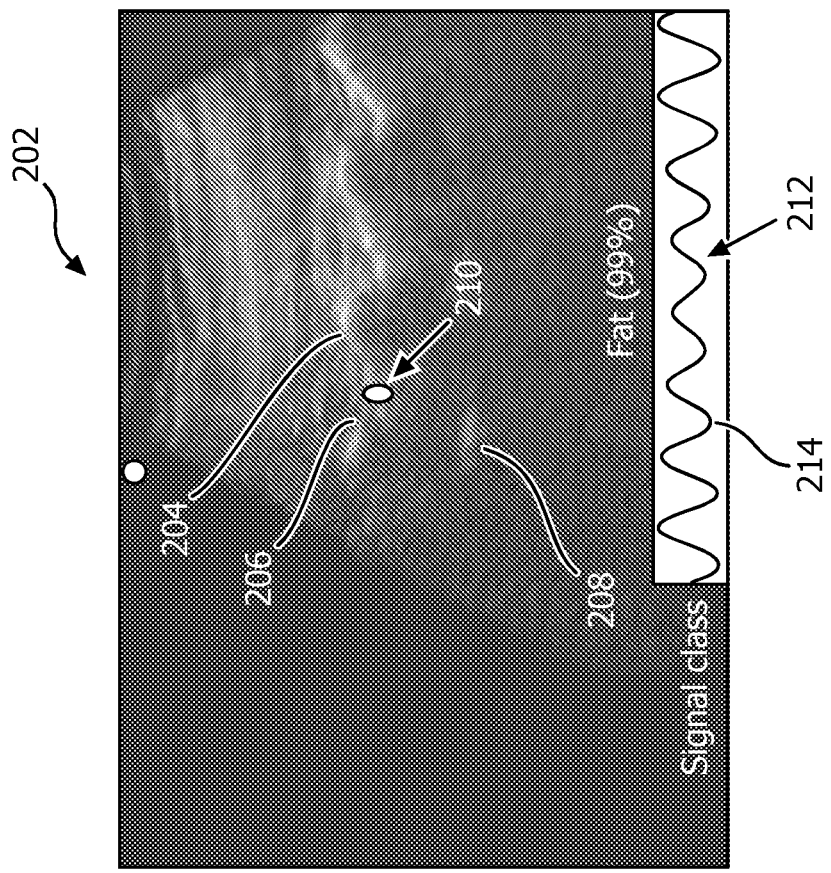
FIG. 2B is an ultrasound image showing a portion of a spine with a needle tip highlighted in accordance with the present principles.
Figure 2A:
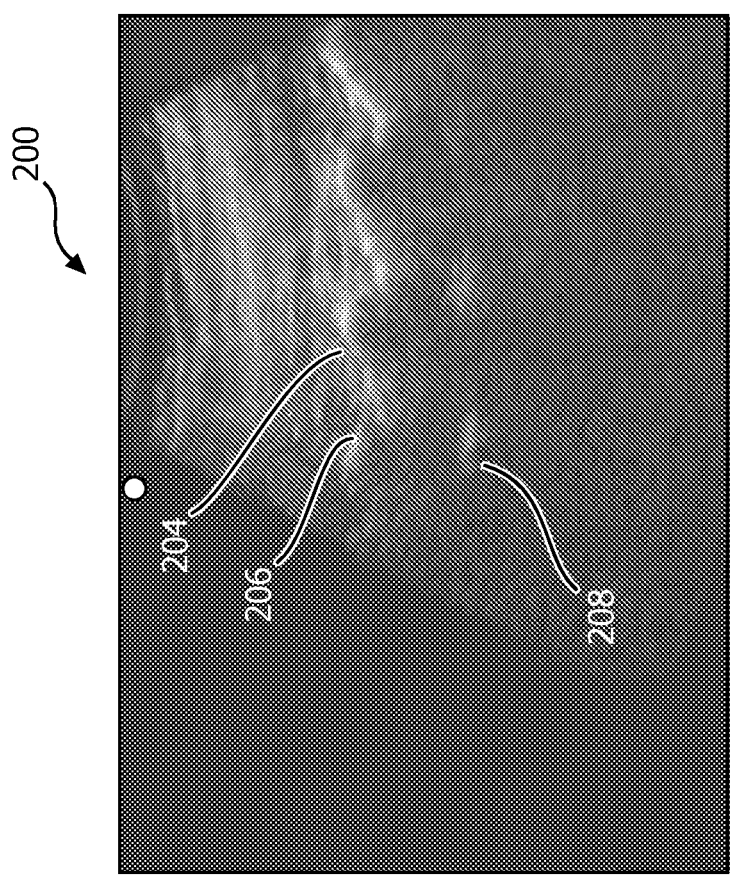
FIG. 2A is an ultrasound image showing a portion of a spine with a needle barely visible.

Referring to FIGS. 2A and 2B, ultrasound images 200 and 202 of the spine are respectively depicted. The images 200 and 202 show a spinal process 204 and ligamentum flavum/posterior dura region 206. In addition, a vertebral body 208 (and/or anterior dura) is identified. In FIG. 2A, a needle is not visible or is hardly visible. In FIG. 2B, the signal processing module or algorithm 150 is employed which highlights a needle tip for precise spatial needle positioning. The needle tip is indicated by a small circle 210 overlaid on the ultrasound image 202. Signal analysis at the needle tip further gives an indication of the type of tissue the needle is in. An overlay 212 includes the circle 210 to highlight the tip of the needle and includes a signal class and tissue indicator 214 that indicates the tissue (e.g., fat is this case) that the tip is embedded in based upon a signal class from the signal analysis.

Figure 3:
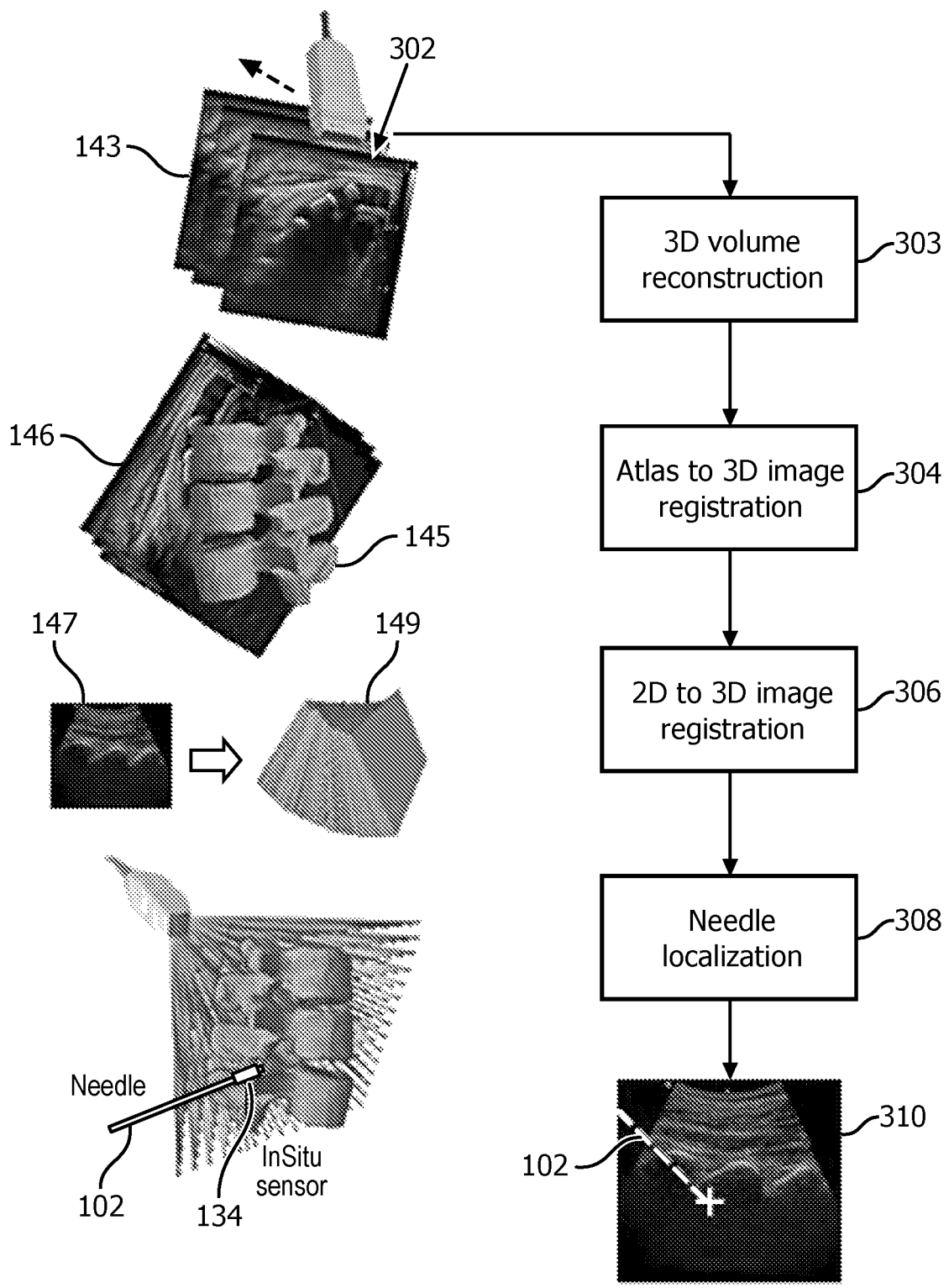
FIG. 3 is a flow diagram showing a method for tracking a penetrating instrument in accordance with illustrative embodiments.

Referring to FIG. 3, a flow diagram shows a method for tracking an instrument in accordance with the present principles. In block 302, a quick sweep in an elevation direction of a linear probe (e.g., an ultrasonic probe) can be employed to construct a 3D volume in block 303 of the patient spinal anatomy from 2D images 143 using, e.g., speckle correlation methods. In block 304, the 3D volume can be then registered to a statistical model, atlas or pre-operative CT images (model 146) of vertebrae 145. This improves the 3D understanding of the anatomy before the intervention. In block 306, a live image 147 (e.g., US image) can now be registered to this 3D plan 149 (including the models, images atlas, etc.) using a slice-volume fusion algorithm. In block 308, an instrument 102 (e.g., needle) is now inserted into the patient and localized. The needle can be tracked in 3D using needle tracking (in-situ) technology (e.g., using an ultrasound transducer 134 or transducers on the needle). In block 310, the in-situ technology is employed to determine the type of tissue the needle is currently passing through or in contact with. This feature provides relevant information in real-time (in-situ) to an operator or technician to provide feedback as to where the needle is penetrating and to provide an indicator when the needle has reached its target depth or position. In addition, an alarm may be triggered in the instance when the needle experiences an unexpected change or varies from a planned trajectory or depth. In block 310, the needle 102 can be visualized on top of a 3D plan or image using an overlay image and signal processing algorithms. The overlay may provide indications of the tissue type or other data relevant to the needle trajectory and depth.

Referring again to block 308, the spatial position of the needle tip with respect to a frame of reference attached to the ultrasound image is known with in-situ technology. In-situ technology refers to the ability to track the needle or instrument along with real-time imaging displays. In particularly useful embodiments, in-situ technology includes the use of one or more sensors, transducers, transponders, etc. mounted on or in the needle or instrument and located at a position of interest on the needle or instrument. In a particularly useful embodiment, a sensor at a needle tip receives signals from the imaging probe as its beams sweep the field of view. The time of arrival of these beams gives the distance of the sensor to the imaging array, and an amplitude profile of the beams gives the lateral or angular distance. Other variants of the same principles can also be employed. For example, the tip sensor may be active and generate its own ultrasound signal, be passive and reflect or transpond a received ultrasound signal.

Figure 4:
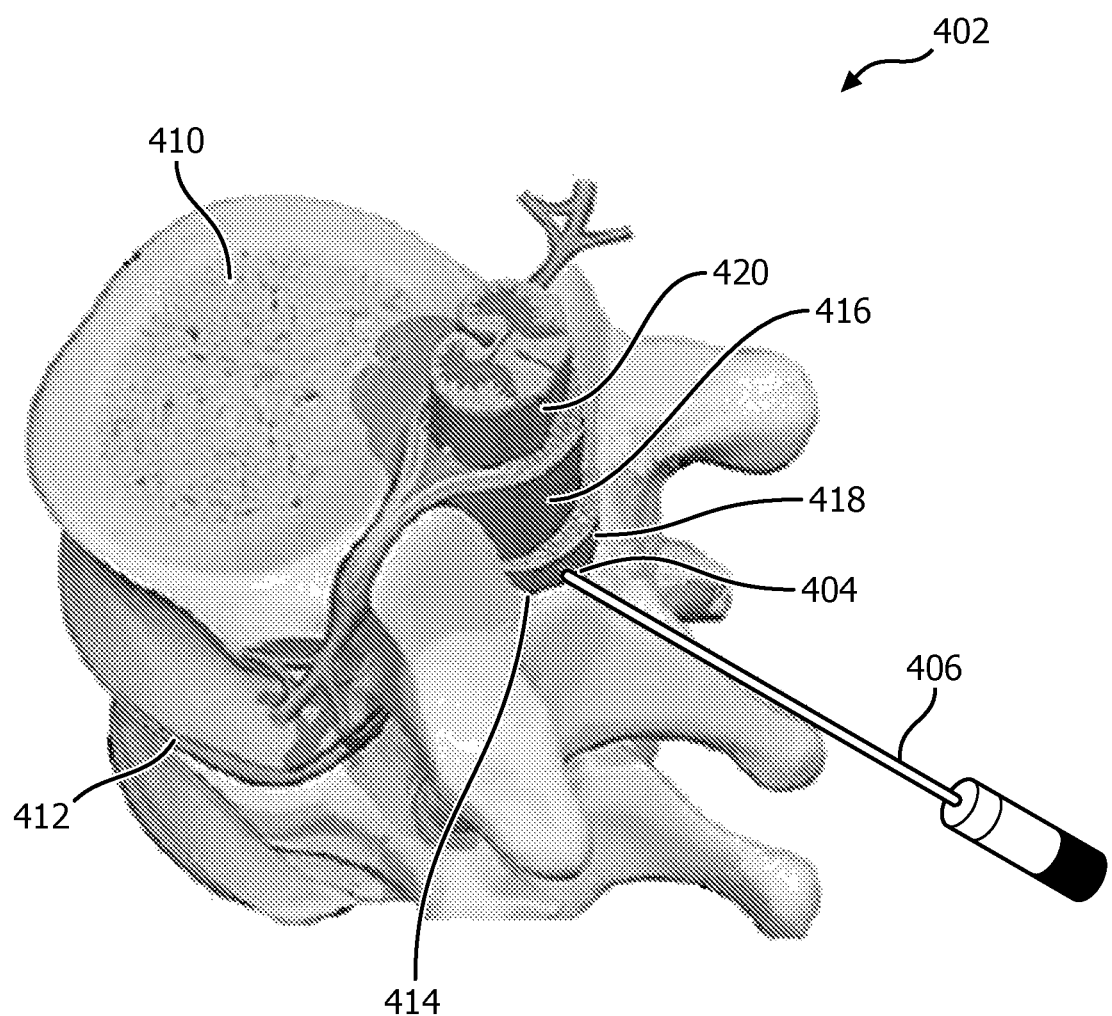
FIG. 4 is a diagram showing a portion of the spine to show an epidural space as a target for needle guidance in accordance with the present principles.

Referring to FIG. 4, a portion of a spine 402 is shown to illustrate an application in accordance with block 310. The spine 402 includes vertebral bodies 410 with intervertebral discs 412 disposed therebetween. An epidural space 414 is an area of space between an outermost tissue layer (dura) 416 and an inside surface of bone 418 and supporting ligaments. The epidural space 414 contains fat tissue along with blood vessels and nerve roots.

A single-element (or multiple element) ultrasound transducer 404 is also preferably employed to measure acoustic characteristics of tissues that surround a tip of a needle 406. Using classification techniques, one can distinguish muscle, ligament, fat, bone and nerve tissue and therefore, notify a clinician once the tip of the needle 406 crosses the ligamentum flavum into the fatty epidural space 414, or warn the physician if the needle 406 is inserted into the spinal cord 420 and avoid devastating complications due to injection of anesthetic unwanted areas.

The transducer 404 at the tip of the needle 406 is preferably used in pulse-echo mode. Its operating frequency is such that it probes a few millimeters of tissue around the transducer 404 (e.g., in the 20 to 40 MHz range). Note that such a high frequency element is easily embedded into a needle because of its small dimensions, and is still able to receive signals from the lower frequency (~3 MHz) imaging probe in the hydrostatic regime. Characteristics of the pulse-echo signal, for example, attenuation of ultrasound as a function of depth and frequency-dependent attenuation as measured by temporal filtering and fitting of the detected envelope of the signal, are employed for signal classification. The characteristics and properties of the various tissues can be characterized in advance and employed for comparison with real-time signals to perform the signal classification. Two orthogonal or angled sensors may also be used to measure anisotropy of the medium (ligaments are highly anisotropic but the epidural space 414 is isotropic).

The presence of a sensor at or near the needle tip, combined with the enhanced display with highlighted and tracked tip position and tissue type classifier, provides a highly reliable tool for injecting an instrument through layers of tissues and avoiding sensitive tissues. Signal processing analysis is used for performing localization and classification to give an operator confidence as to a position of the needle or instrument. In particularly useful examples, needle insertion under ultrasound guidance (making use of both needle localization and tissue differentiation modules or using only the tissue differentiation module) can be employed for pain management and regional anesthesia procedures, biopsies of all kinds including cancer biopsies, amniocentesis, spinal tap, vascular access, drainage procedures, etc.

Figure 5:
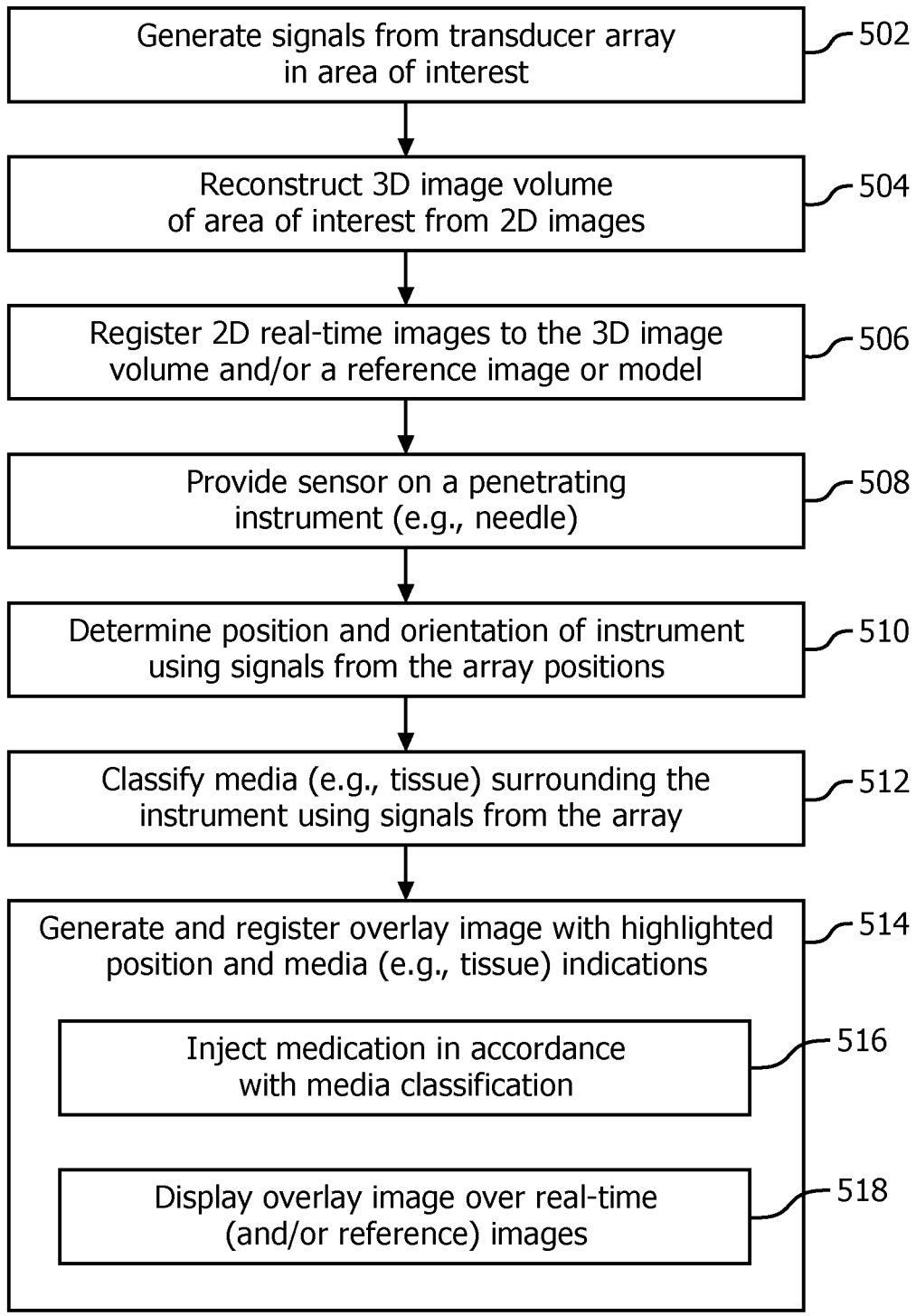
FIG. 5 is another flow diagram showing another method for tracking a penetrating instrument in accordance with illustrative embodiments.

Referring to FIG. 5, another embodiment for tracking a penetrating instrument is shown. In block 502, signals from a plurality of array positions are generated to provide one or more real-time images of an area of interest. In useful embodiments, the real-time images are collected ultrasonically. The ultrasonic images may include two-dimensional images and may need to be reconstructed to form three dimensional volumes. Three dimensional ultrasound images may also be employed. In block 504, a three-dimensional image volume of the area of interest may be reconstructed from two-dimensional images for the one or more real-time images. In block 506, two-dimensional images taken in real-time may be registered to the three-dimensional image volume of the area of interest and/or a reference image (atlas, image, model, etc.) to improve instrument visualization. In one embodiment, the reference image may include a vertebra or vertebrae (or other bone(s)).

In block 508, a penetrating instrument having a body with at least one sensor mounted at a position of interest on the body is provided. The sensor is responsive to the signals from the plurality of array positions.

In block 510, a position and orientation of the penetrating instrument is determined in accordance with the signals from the plurality of array positions using a signal processing module. In one embodiment, the sensor for the penetrating instrument is configured to measure time of flight from the plurality of array positions to determine the position and orientation of the penetrating instrument. In block 512, media in which the position of interest is positioned is classified based upon a response of the sensor to the signals from the plurality of array positions. In block 514, an overlay image is generated and registered to the one or more real-time images to identify a position of the position of interest and provide feedback on the media in which the position of interest is positioned. The position is preferably highlighted in the overlay image, and the media (e.g., tissue type) may be indicated in the overlay image. In block 516, the penetrating instrument may include a needle, the position of interest may include a distal tip of the needle and the media may include a tissue type. Material, such as pain medications, may be injected through the needle when a selected tissue type is indicated in the overlay image. For example, in the case where an epidural needle is employed, when fatty tissue is encountered after ligament tissue, the epidural space is reached and medication may be administered. In block 518, the overlay image is displayed on the one or more real-time images.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for penetrating instrument guidance in epidural interventions using smart needles and advanced image fusion (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for tracking a penetrating instrument, comprising:
an ultrasound transducer array configured to generate ultrasound signals from a plurality of array positions and to provide one or more real-time images of an area of interest;
a penetrating instrument having a body with at least one ultrasound transducer mounted at a position of interest on the body, the at least one ultrasound transducer being responsive to the ultrasound signals generated by the plurality of array positions;
a signal processing module configured to determine a position and orientation of the penetrating instrument in accordance with the ultrasound signals generated by the plurality of array positions based upon a response of the at least one ultrasound transducer to the ultrasound signals generated by the plurality of array positions, the signal processing module being further configured to classify media in which the position of interest is positioned based on pulse-echo mode signals transduced by the at least one ultrasound transducer, wherein the pulse-echo mode signals are configured to measure acoustic characteristics of surrounding tissue;
an overlay module configured to generate an overlay image registered to the one or more real-time images to identify a position of the position of interest and provide visual feedback on the classification of the media in which the position of interest is positioned; and
a display configured to provide the visual feedback of the overlay image on the one or more real-time images.

2. The system as recited in claim 1, wherein the ultrasound transducer array includes ultrasound transducers and the one or more real-time images include two-dimensional images, the system further comprising:
a three-dimension reconstruction module configured to reconstruct a three-dimensional image volume of the area of interest from the two-dimensional images.

3. The system as recited in claim 2, further comprising a registration module configured to register at least one of (i) two-dimensional real-time images to the three-dimensional image volume of the area of interest, or (ii) a reference image to the three-dimensional image volume of the area of interest.

4. The system as recited in claim 1, wherein the penetrating instrument includes a needle and the position of interest includes a distal tip of the needle.

5. The system as recited in claim 4, wherein the signal processing module is configured to classify a tissue type of the media and classification of the tissue type indicates when material should be injected through the needle into the media by indicating when a target tissue type for the material is reached by the penetrating instrument.

6. The system as recited in claim 5, wherein the tissue type is displayed in the overlay image to indicate to indicate when to inject material through the needle.

7. The system as recited in claim 1, wherein the at least one ultrasound transducer of the penetrating instrument is configured to measure time of flight from the plurality of array positions to determine the position and orientation of the penetrating instrument.

8. The system as recited in claim 1, wherein the penetrating instrument includes a needle, the position of interest includes a distal tip of the needle and the media includes a tissue type, the method further comprising injecting material through the needle when a selected tissue type is indicated in the overlay image by indicating when a target tissue type for the material is reached by the distal tip of the needle.

9. A system for tracking a penetrating instrument having an ultrasound transducer mounted at or near a distal tip position based on ultrasound signals generated by a plurality of array positions of an ultrasound transducer array, the system comprising:
a signal processing module configured to:
determine a position and orientation of a penetrating instrument in accordance with the ultrasound signals generated by the plurality of array positions and the ultrasound signals received by the at least one transducer; and to
classify a tissue type in which the tip of the penetrating instrument is positioned based on pulse-echo mode signals transduced by the at least one ultrasound transducer, wherein said pulse-echo mode signal arc configured to measure acoustic characteristics of surrounding tissue.

10. The system as recited in claim 9, further comprising:
an ultrasound transducer array configured to generate the ultrasound signals generated by the plurality of array positions to provide one or more real-time images of an area of interest.

11. The system as recited in claim 10, further comprising:
an overlay module configured to generate an overlay image registered to the one or more real-time images, the overlay image including a highlighted position of the penetrating instrument and visual feedback corresponding to the classification of the tissue type.

12. The system as recited in claim 11, further comprising:
a display configured to provide the visual feedback of the overlay image on the one or more real-time images.

13. The system as recited in claim 12, wherein the one or more real-time images include one or more two-dimensional images, the system further comprising:
a three-dimension reconstruction module configured to reconstruct a three-dimensional image volume of the area of interest from the one or more two-dimensional images.

14. The system as recited in claim 13, further comprising a registration module configured to register one or more two-dimensional real-time images to the three-dimensional image volume of the area of interest.

15. The system as recited in claim 14, wherein the registration module is further configured to register a reference image to the three-dimensional image volume of the area of interest.

16. The system as recited in claim 9, wherein the penetrating instrument comprises a needle.

17. The system as recited in claim 9, wherein the classification of the tissue type indicates when material should be injected through the penetrating instrument by indicating when a target tissue type for the material is reached by the penetrating instrument.

18. The system as recited in claim 9, wherein the penetrating instrument is tracked for an epidural intervention.

19. A method for tracking a penetrating instrument under control of a workstation, the method comprising:
generating signals from a plurality of array positions of an intraoperative ultrasound transducer array to generate one or more real-time images of an area of interest;
determining a position and orientation of a penetrating instrument in accordance with the signals generated by the plurality of array positions using a signal processing module, the penetrating instrument having a body with at least one ultrasound transducer mounted at a position of interest on the body, the at least one ultrasound transducer being responsive to the ultrasound signals generated by the plurality of array positions;
classifying media in which the position of interest is positioned based upon pulse-echo mode signals transduced by the at least one ultrasound transducer by measuring acoustic characteristics of surrounding tissue;
generating an overlay image registered to the one or more real-time images using an overlay module to identify a position of the position of interest and provide visual feedback on the classification of the media in which the position of interest is positioned; and
displaying the visual feedback of the overlay image on the one or more real-time images.

20. The method as recited in claim 19, further comprising:
reconstructing a three-dimensional image volume of the area of interest from two-dimensional images for the one or more real-time images; and
registering two-dimensional images taken in real-time to the three-dimensional image volume of the area of interest and/or a reference image.

* * * * *